US011559596B2

(12) United States Patent
Harris et al.

(10) Patent No.: US 11,559,596 B2
(45) Date of Patent: Jan. 24, 2023

(54) VEHICLE DOOR HANDLE SANITIZING SYSTEM

(71) Applicant: Toyota Motor Engineering & Manufacturing North America, Inc., Plano, TX (US)

(72) Inventors: Ryan C. Harris, Saline, MI (US); Scott Louis Frederick, Brighton, MI (US)

(73) Assignee: Toyota Motor Engineering & Manufacturing North America, Ino., Plano, TX (US)

( * ) Notice: Subject to any disclaimer, the term of this patent is extended or adjusted under 35 U.S.C. 154(b) by 293 days.

(21) Appl. No.: 16/905,304

(22) Filed: Jun. 18, 2020

(65) Prior Publication Data

US 2021/0393831 A1 Dec. 23, 2021

(51) Int. Cl.

| | |
|---|---|
| ***A61L 2/24*** | (2006.01) |
| ***A61L 2/22*** | (2006.01) |
| ***E05B 1/00*** | (2006.01) |
| ***E05B 79/06*** | (2014.01) |
| ***E05B 85/16*** | (2014.01) |

(52) U.S. Cl.

CPC ................... *A61L 2/22* (2013.01); *A61L 2/24* (2013.01); *E05B 79/06* (2013.01); *E05B 85/16* (2013.01); *A61L 2202/14* (2013.01); *A61L 2202/15* (2013.01); *A61L 2202/16* (2013.01); *E05Y 2600/46* (2013.01); *E05Y 2900/531* (2013.01)

(58) Field of Classification Search

CPC ............. A61L 2/22; A61L 2/24; E05B 1/0069

See application file for complete search history.

(56) References Cited

U.S. PATENT DOCUMENTS

| | | | | |
|---|---|---|---|---|
| 7,360,674 | B2 | 4/2008 | Sassoon | |
| 11,318,960 | B1 * | 5/2022 | McKnew | G01C 21/3415 |
| 2006/0153733 | A1 * | 7/2006 | Sassoon | A61L 2/18 422/292 |
| 2012/0251387 | A1 * | 10/2012 | Samaras | E05B 1/0069 422/292 |
| 2015/0190538 | A1 | 7/2015 | Olvera et al. | |
| 2017/0129396 | A1 * | 5/2017 | Salter | B60Q 3/20 |
| 2017/0173200 | A1 | 6/2017 | Wyman et al. | |

FOREIGN PATENT DOCUMENTS

DE 102012214780 A1 * 2/2014 ............... A61L 2/22

OTHER PUBLICATIONS

English Translation of International Document No. DE 102015014223 A1 provided by the European Patent Office website espacenet.com: Krass; Door Handle Device for Side Door of Motor Vehicle; May 12, 2016 (Year: 2016).*

* cited by examiner

*Primary Examiner* — Kevin Joyner

(74) *Attorney, Agent, or Firm* — Christopher G. Darrow; Darrow Mustafa PC

(57) ABSTRACT

A vehicle door assembly comprising includes a vehicle door panel, a vehicle door handle operably connected to the door panel so as to enable operation of a door latch by the door handle, and at least one sanitizer dispensing mechanism having at least a first nozzle coupled to the vehicle door panel and structured to discharge a sanitizing material onto an exterior surface of the door handle.

14 Claims, 3 Drawing Sheets

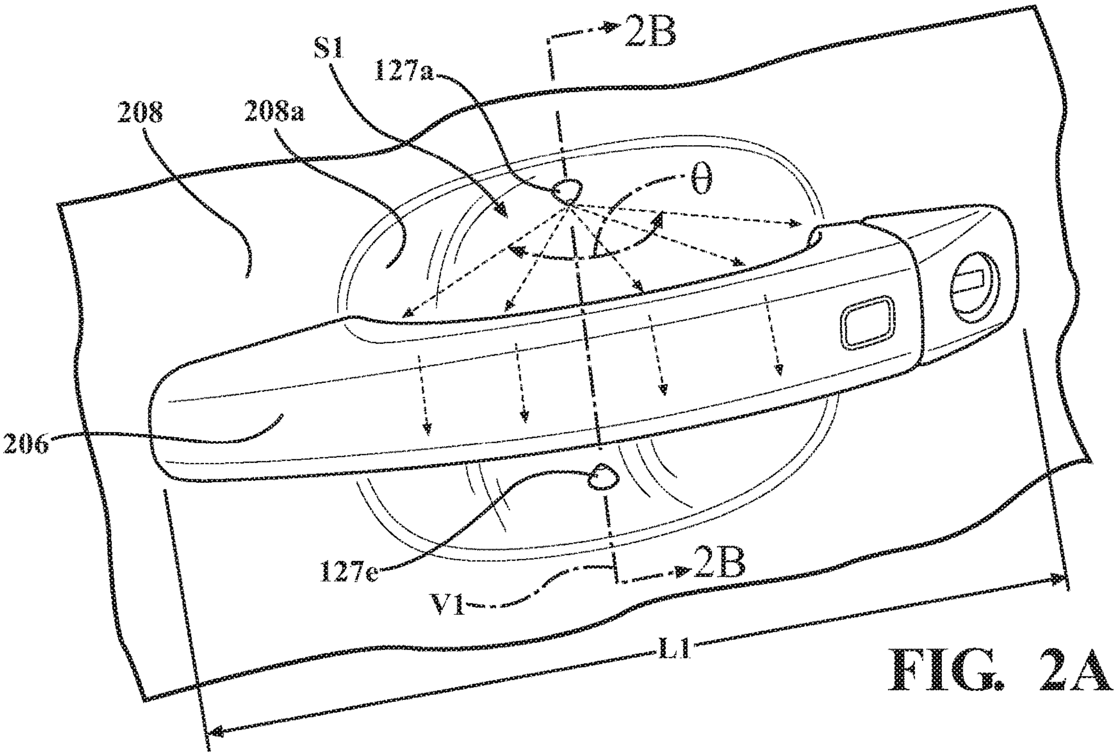
FIG. 2A
FIG. 2B
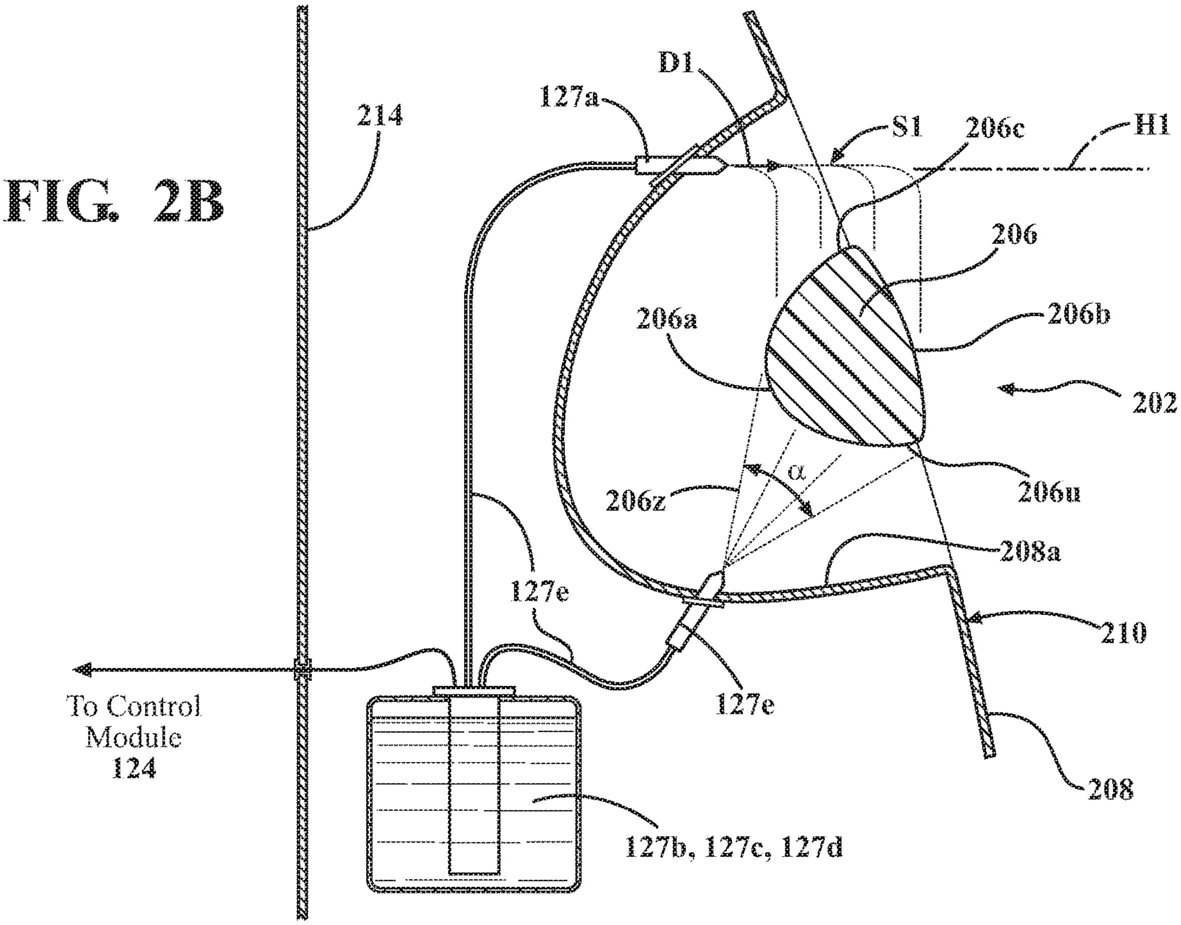

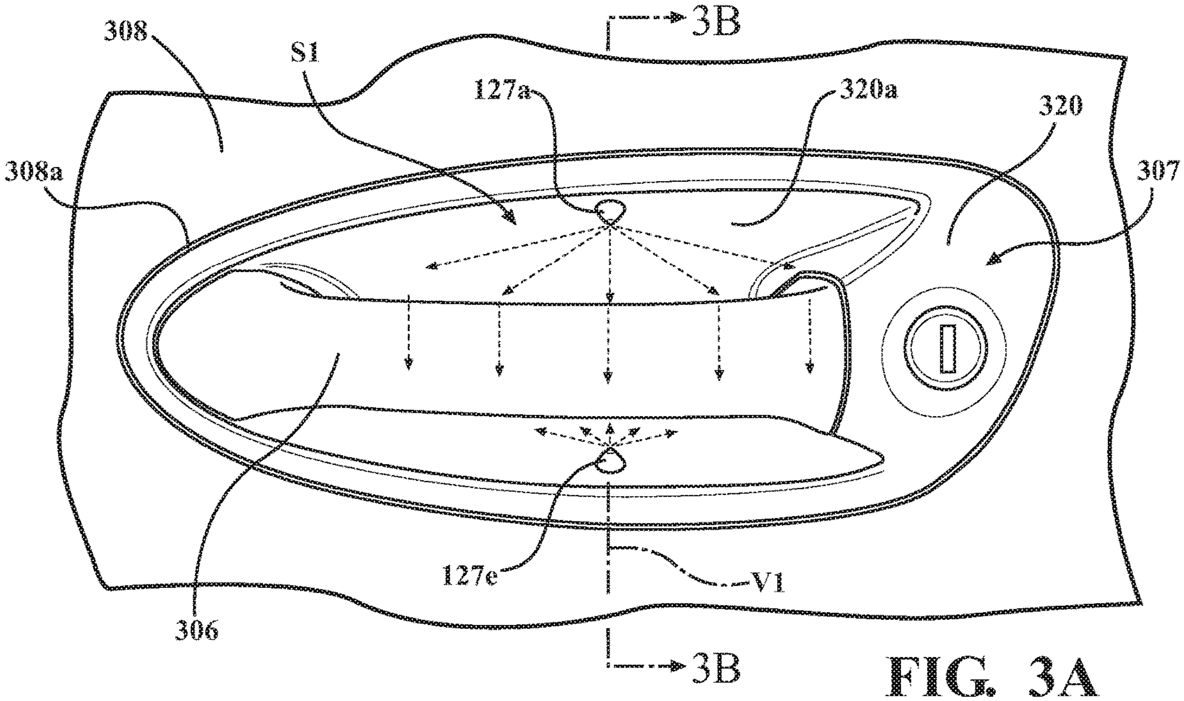
FIG. 3A
FIG. 3B
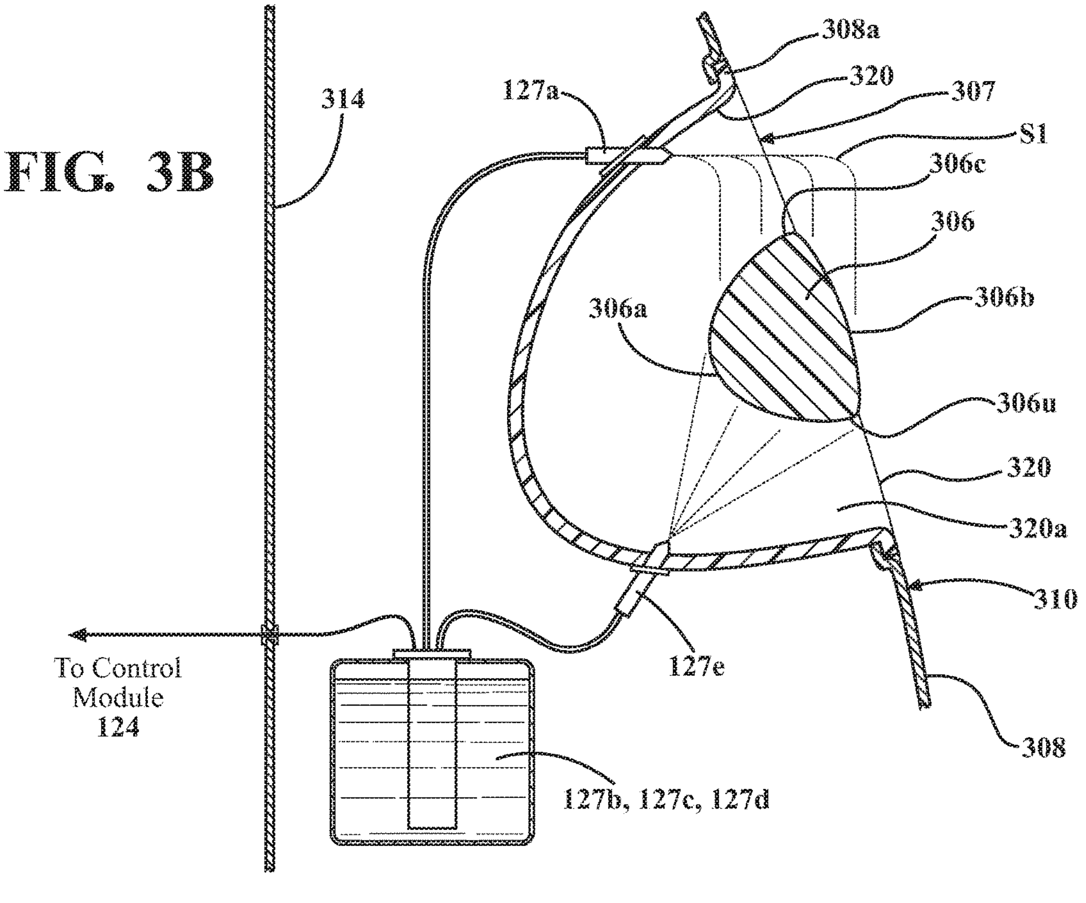

VEHICLE DOOR HANDLE SANITIZING SYSTEM

TECHNICAL FIELD

The subject matter described herein relates to sanitizing systems and, more particularly, to a system for sanitizing a vehicle door handle after use.

BACKGROUND

It is increasingly important for both medical and psychological reasons for people to feel that surfaces they touch will be sanitized to cleanse bacteria and viruses from the surfaces. Numerous users may come grasp handles of vehicle doors on a frequent basis. These handles may be rarely sanitized after use, and it may be burdensome for vehicle owners to manually wipe-down door handles after every use.

SUMMARY

In one aspect of the embodiments described herein, a vehicle door assembly comprising includes a vehicle door panel, a vehicle door handle operably connected to the door panel so as to enable operation of a door latch by the door handle, and at least one sanitizer dispensing mechanism having at least a first nozzle coupled to the vehicle door panel and structured to discharge a sanitizing material onto an exterior surface of the door handle.

BRIEF DESCRIPTION OF THE DRAWINGS

The accompanying drawings, which are incorporated in and constitute a part of the specification, illustrate various systems, methods, and other embodiments of the disclosure. It will be appreciated that the illustrated element boundaries (e.g., boxes, groups of boxes, or other shapes) in the figures represent one embodiment of the boundaries. In some embodiments, one element may be designed as multiple elements or multiple elements may be designed as one element. In some embodiments, an element shown as an internal component of another element may be implemented as an external component and vice versa. Furthermore, elements may not be drawn to scale.

FIG. 2A is a schematic side view of a portion of a vehicle door assembly in accordance with an embodiment described herein, showing a door handle mounted to an exterior door panel opposite a recess in the door panel.

FIG. 2B is a schematic cross-sectional side view of the portion of a vehicle door assembly shown in FIG. 2A including spray nozzles of an embodiment of a sanitizer dispensing mechanism mounted to the exterior door panel within the recess.

FIG. 3A is a schematic side view of a portion of a vehicle door assembly in accordance with another embodiment described herein, showing a door handle incorporated into a door handle module mounted to the door in an opening formed in the exterior door panel.

FIG. 3B is a schematic cross-sectional side view of the portion of a vehicle door assembly shown in FIG. 3A including spray nozzles of a sanitizer dispensing mechanism mounted in a cavity of a housing of the door handle module.

DETAILED DESCRIPTION

Embodiments described herein relate to a vehicle door assembly including a vehicle door panel, a vehicle door handle operably connected to the door panel so as to enable operation of a door latch by the door handle, and at least one sanitizer dispensing mechanism having at least a first nozzle coupled to the vehicle door panel and structured to discharge a sanitizing material onto exterior surfaces of the door handle. Multiple spray nozzles may be used to cover key surfaces of the door handle. The dispensing mechanism may be configured to operate autonomously to spray different surfaces of the door handle with sanitizer following passage of a predetermined period of time after a user has either latched or locked the door.

Figure 1A:
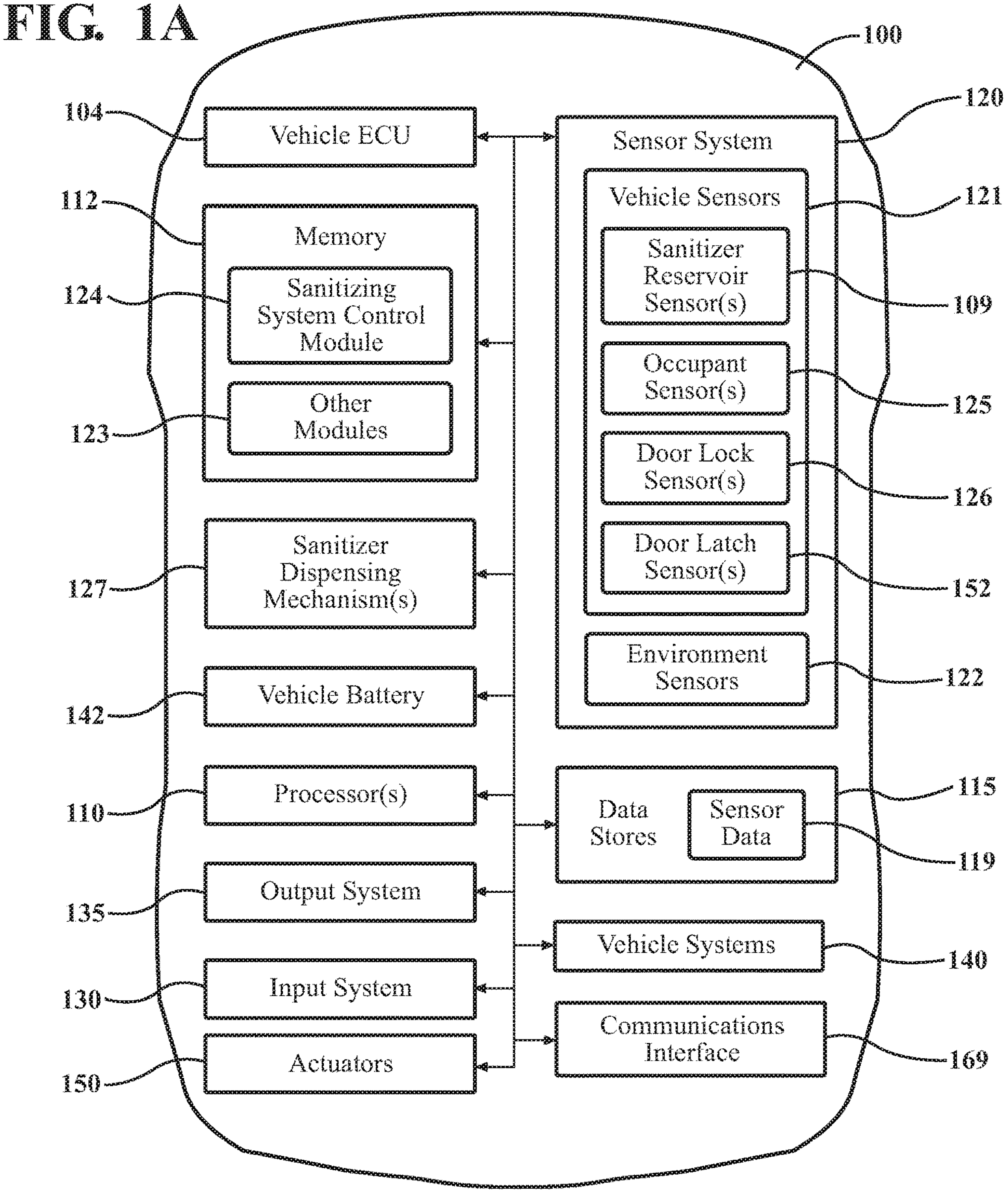
FIG. 1A is a block schematic diagram of a vehicle incorporating an autonomous vehicle door handle sanitizing system in accordance with embodiments described herein.

FIG. 1A is a block schematic diagram of a vehicle 100 incorporating an autonomous vehicle door handle sanitizing system in accordance with embodiments described herein. As used herein, a "vehicle" is any form of motorized transport. In one or more implementations, the vehicle 100 is a conventional passenger vehicle. Various operations of the vehicle may be controlled by an electronic control unit (ECU) 104 and/or a memory 112 including one or more specialized modules as described herein. While arrangements will be described herein with respect to passenger vehicles, it will be understood that embodiments are not limited to passenger vehicles. In some implementations, the vehicle 100 may be any form of motorized transport that benefits from the functionality discussed herein.

The vehicle 100 also includes various elements. It will be understood that in various embodiments it may not be necessary for the vehicle 100 to have all of the elements shown in FIG. 1A. The vehicle 100 can have any combination of the various elements shown in FIG. 1A. Further, the vehicle 100 can have additional elements to those shown in FIG. 1A. In some arrangements, the vehicle 100 may be implemented without one or more of the elements shown in FIG. 1A. While the various elements are shown as being located within the vehicle 100 in FIG. 1A, it will be understood that one or more of these elements can be located external to the vehicle 100.

Some of the possible elements of the vehicle 100 are shown in FIG. 1A and will be described with reference thereto. Additionally, it will be appreciated that for simplicity and clarity of illustration, where appropriate, reference numerals may have been repeated among the different figures to indicate corresponding or analogous elements. In addition, the discussion outlines numerous specific details to provide a thorough understanding of the embodiments described herein. Those of skill in the art, however, will understand that the embodiments described herein may be practiced using various combinations of these elements.

The vehicle 100 can include one or more processors 110. In one or more arrangements, the processor(s) 110 can be a main processor(s) of the vehicle 100. For instance, the processor(s) 110 can be an electronic control unit (ECU) for the vehicle. The vehicle 100 can include one or more data stores 115 for storing one or more types of data. The data store(s) 115 can include volatile and/or non-volatile memory. Examples of suitable data store(s) 115 include RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The data store(s) 115 can be a component of the processor(s) 110, or the data store(s) 115 can be operably connected to the processor(s) 110 for use thereby. The term "operably connected," as used throughout this description, can include direct or indirect connections, including connections without direct physical contact.

The one or more data store(s) 115 can include sensor data 119. In this context, "sensor data" means any information about the sensors that the vehicle 100 is equipped with, including the capabilities and other information about such sensors. As will be explained below, the vehicle 100 can include the sensor system 120. The sensor data 119 can relate to one or more sensors of the sensor system 120. As an example, in one or more arrangements, the sensor data 119 can include information on one or more vehicle door lock sensors 126 of the sensor system 120.

As noted above, the vehicle 100 can include the sensor system 120. The sensor system 120 can include one or more sensors. "Sensor" means any device, component and/or system that can detect, and/or sense something. The one or more sensors can be configured to detect, and/or sense in real-time. As used herein, the term "real-time" means a level of processing responsiveness that a user or system senses as sufficiently immediate for a particular process or determination to be made, or that enables the processor to keep up with some external process. In arrangements in which the sensor system 120 includes a plurality of sensors, the sensors can work independently from each other. Alternatively, two or more of the sensors can work in combination with each other. In such case, the two or more sensors can form a sensor network. The sensor system 120 and/or the one or more sensors can be operably connected to the processor(s) 110, the data store(s) 115, and/or other element(s) of the vehicle 100 (including any of the elements shown in FIG. 1A).

The sensor system 120 can include any suitable type of sensor. Various examples of different types of sensors will be described herein. However, it will be understood that the embodiments are not limited to the particular sensors described. Various examples of sensors of the sensor system 120 are described herein. The example sensors may be part of the one or more environment sensors 122 and/or the one or more vehicle sensors 121. However, it will be understood that the embodiments are not limited to the particular sensors described. The sensor system 120 may include any sensors suitable for and/or required to enable performance any of the data acquisition and/or vehicle control operations contemplated herein.

Sensors of sensor system 120 may be communicably coupled to the various systems and components of the vehicle 100. Sensor system 120 may include sensors configured to detect the current state or status of vehicle systems and components and to generate indications (for example, using trouble codes) possible malfunctions of vehicle systems and components.

Sensors of the sensor system 120 may include (or be operably connected to) one or more timers or clocks (not shown) configured to enable acquisition, tracking, storage, generation and/or processing of time-correlated sensor data. That is, data acquired by the sensors described herein may be monitored and recorded over one or more predetermined time periods to determine time-related variations in the parameters monitored by the sensors. For example, a timer may be activated by closing and latching and/or locking of a vehicle door to enable measurement of a predetermined time period after latching and/or locking of the door, prior to dispensing a quantity of sanitizer onto the door handle as described herein.

The sensor system 120 can include one or more vehicle sensors 121. The vehicle sensor(s) 121 can detect, determine, and/or sense information about the vehicle 100 itself and/or any occupants inside the vehicle. The vehicle sensor(s) 121 may include sensors configured to detect conditions and/or events inside the vehicle interior or occupant compartment. The vehicle sensor(s) 121 can be configured to detect, and/or sense one or more characteristics of the vehicle 100, such as the status (latched or unlatched, locked or unlocked, etc.) of one or more vehicle doors. The vehicle sensor(s) 121 may include sensors configured to sense aspects of the vehicle mechanical and electrical components and/or systems, to aid in determining a mechanical condition of the vehicle and existing and/or potential problems with the vehicle. For example, reservoir sensors incorporated into or communicably coupled to associated sanitizer reservoirs of the vehicle door handle sanitizing system may detect a level of sanitizer in each reservoir. The vehicle door handle sanitizing system control module 124 descried herein may be configured to cause generation of an alert signal responsive to an amount of sanitizer in the reservoir falling below a certain level. In one or more arrangements, reservoir fill ports (not shown) may be provided along an exterior surface of an inner door panel to enable the sanitizer to be replenished in the reservoir. Each fill port may be connected to an associated reservoir by tubing for example.

The sensor system 120 can include one or more environment sensors 122 configured to acquire data of at least a portion of the external environment of the vehicle 100 (e.g., nearby objects). The environment sensors 122 may detect data or information about the external environment in which the vehicle is located or one or more portions thereof. In one or more arrangements, the environment sensors 122 can include one or more radar sensors, one or more LIDAR sensors, one or more cameras, and/or other types of sensors.

The vehicle wireless communications interface 169 may be configured to enable and/or facilitate communication between the components and systems of the vehicle 100 and entities (such as cloud facilities, cellular and other mobile communications devices, other vehicles, remote servers, pedestrians, etc.) exterior of the vehicle. Wireless communications interface 169 may be configured to facilitate, establish, maintain, and end wireless V2V and V2X communications with any extra-vehicular entity, for example other connectibly-configured vehicles and connected vehicles, pedestrians, servers and entities located in the cloud, edge servers, and other information sources and entities. Information such as sensor data, traffic information, road condition information, weather information, and other types of information may be transmitted and received via the communications interface 169. If required, wireless communications interface 169 may incorporate or be in communication with any network interfaces needed to communicate with any extra-vehicular entities and/or networks. The wireless communications interface may be configured to enable wireless communication between a user mobile device and a vehicle door handle sanitizing system control module 124 as described herein, to enable operating commands to be sent remotely to the vehicle door handle sanitizing system.

The vehicle 100 can include an input system 130. An "input system" includes any device, component, system, element or arrangement or groups thereof that enable information/data to be entered into a machine. For example, the input system 130 may include a keypad, a touch screen or other interactive display, a voice-recognition system and/or any other device or system which facilitates communications between a user and the vehicle. The input system 130 can receive an input from a vehicle occupant (e.g., a driver or a passenger) or a user located remotely from the vehicle 100, for example, using a mobile device. The vehicle 100 can also include an output system 135. An "output system" includes any device, component, or arrangement or groups thereof that enable information/data to be presented to a vehicle occupant (e.g., a driver, a vehicle passenger, etc.) or a remote user. The input and output systems may enable a user to specify the operating parameters of a vehicle door handle sanitizing system as described herein.

The vehicle 100 can include one or more vehicle systems, collectively designated 140. Various examples of the one or more vehicle systems 140 are described herein. However, the vehicle 100 can include more, fewer, or different vehicle systems. It should be appreciated that although particular vehicle systems are separately defined, each or any of the systems or portions thereof may be otherwise combined or segregated via hardware and/or software within the vehicle 100. The vehicle systems 140 can include any or all of a variety of systems usually incorporated into a conventional passenger vehicle, for example, a propulsion system, a braking system, a steering system, throttle system, a suspension system, a transmission system, and/or a navigation system. Each of these systems can include one or more devices, components, and/or a combination thereof, now known or later developed.

The vehicle 100 can include one or more actuators 150. The actuators 150 can be any element or combination of elements operable to modify, adjust and/or alter one or more of the vehicle systems 140 or components thereof to responsive to receiving signals or other inputs from the processor(s) 110, any of the modules stored in memory 112, and/or any other vehicle components or systems, including elements of one or more sanitizer dispensing mechanisms as described herein. Any suitable actuator can be used. For instance, the one or more actuators 150 can include motors, pneumatic actuators, hydraulic pistons, relays, solenoids, and/or piezoelectric actuators, just to name a few possibilities.

Referring now to FIGS. 2A and 2B, vehicle 100 may incorporate at least one vehicle door assembly 202 including an embodiment of a sanitizer dispensing mechanism 127 as described herein. FIG. 2A is a schematic side view of a portion of a vehicle door assembly 202 in accordance with an embodiment described herein, showing a door handle 206 mounted to an exterior door panel 208 opposite a recess 208*a* in the door panel. FIG. 2B is a schematic cross-sectional side view of the portion of a vehicle door assembly 202 shown in FIG. 2A including spray nozzles 127*a* and 127*e* of an embodiment of a sanitizer dispensing mechanism 127 mounted to the exterior door panel 208 within the recess 208*a*.

In one or more arrangements, the vehicle door assembly 202 may include a vehicle door 210 having a vehicle door panel 208 and a vehicle door handle 206 operably connected to the door panel 208 so as to enable operation of a door latch (not shown) by the door handle. The vehicle door panel 208 may be an exterior door panel (i.e., a panel facing and positioned along an exterior of the vehicle). The door assembly 202 may also include an interior door panel 214 secured to the exterior door panel 208 and structured to face an occupant compartment of the vehicle when the vehicle door assembly 202 is incorporated into the vehicle 100.

Figure 1B:
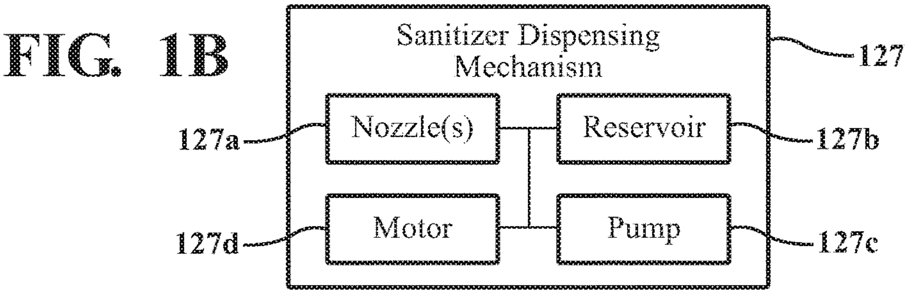
FIG. 1B is a block schematic diagram of a sanitizer dispensing mechanism in accordance with an embodiment described herein.

The door assembly 202 may include at least one sanitizer dispensing mechanism 127. FIG. 1B is a schematic block diagram of an exemplary embodiment of a sanitizer dispensing mechanism. Elements of the sanitizer dispensing mechanism 127 may be mounted inside the door 210 between the exterior door panel 208 and the interior door panel 214. The sanitizer dispensing mechanism 127 may include at least a first nozzle 127*a* coupled to the vehicle door panel 208 and structured to discharge a sanitizing material onto an exterior surface of the door handle 206. In one or more arrangements, the first nozzle 127*a* may be an atomizer structured to dispense a fine mist of sanitizing material. A sanitizer reservoir 127*b* in fluid communication with the nozzle 127*a* may store a quantity of hand sanitizer product to be dispensed onto the door handle 206. A motor 127*d* may power a pump 127*c* structured to move the sanitizer from the reservoir 127*b* to the nozzle 127*a*, where the sanitizer is discharged from the nozzle. The motor 127*d* and pump 127*c* may be combined into a single unit. The motor/pump may be powered by the vehicle battery 142 or by any other suitable means. Suitable flexible tubing may connect the reservoir and the nozzle 127*a*.

In the embodiment shown in FIGS. 2A and 2B, the door panel 208 includes a recess 208*a* structured to receive at least a portion of the door handle 206 therein when the door handle is mounted to the door 210. The recess 208*a* is provided to enable a user to grip the handle 206 along an innermost exterior surface 206*a* of the door handle (i.e., a surface of the door handle closest to an occupant compartment of the vehicle 100). In the embodiment shown in FIGS. 2A and 2B, the first nozzle 127*a* (and any additional nozzles of the sanitizer dispensing mechanism) are mounted within the recess 208*a*. The door handle 206 may project outwardly from the recess 208*a* to a degree depending upon a particular vehicle design.

In embodiments described herein, the first nozzle 127*a* may be structured to dispense sanitizing material onto all or most of the surfaces of the door handle 206 most likely to be contacted by a user's hand. For example, the first nozzle 127*a* may be structured to dispense sanitizing material onto an outermost exterior surface 206*b* of the door handle 206. An outermost exterior surface 206*b* of the door handle 206 may be a surface of the door handle located farthest from an occupant compartment of the vehicle 100. The first nozzle 127*a* may also be structured to dispense sanitizing material onto the innermost exterior surface 206*a* of the door handle. Because this surface 206*a* may be touched by fingers of a user gripping the handle 206, it may be desirable to sanitize this surface.

In one or more arrangements, to apply sanitizer to the above-mentioned surfaces of the door handle 206, the first nozzle 127*a* may be structured to dispense the sanitizing material in an arcuate distribution from the first nozzle along a horizontal plane H1 located vertically above the door handle 206 when the vehicle door assembly 202 is mounted on the vehicle 100. To this end, the first nozzle 127*a* may be structured to reside at a level vertically higher than the door handle 206 when the vehicle door assembly 202 is mounted on the vehicle. The angle θ over which the sanitizer is distributed may be varied according to such factors as the distance of the door handle 206 from the nozzle 127*a* and the length of the door handle 206. As seen in FIGS. 2A and 2B, the spray pattern Si emanating from the first nozzle 127*a* may extend out to varying distances from the nozzle, after which a portion of the dispensed sanitizer may fall onto the each of an uppermost surface (i.e., vertically highest) 206*c*, the innermost surface 206*a*, and the outermost surface 206*b* of the door handle 206. Liquid falling on uppermost surface 206*c* may also flow down along the door handle to surfaces 206*a*, 206*b*, and 206*u*. In addition, as shown in FIG. 2A, the first nozzle 127*a* may be positioned along a vertical plane V1 bisecting or substantially bisecting a length L1 of the door handle 206. These arrangements may help ensure that sanitizer is applied to the desired surfaces along most of the length of the door handle 206, and along portions of the most likely to be touched by a user.

Referring to FIGS. 3A and 3B, in one or more alternative arrangements, a door 310 may include a vehicle outer door panel 308 with an opening 308*a* formed therein, and an inner door panel 314 secured to the outer door panel 308. The door handle 306 may be mounted in a door handle module 307 which may be received and secured in the opening 308*a*. The door handle 306 may then be operably connected to an associated door latch mechanism (not shown) in a conventional manner. The door handle module 307 may include a housing 320 defining a recess 320*a* into which at least a portion of the door handle 306 may reside when the handle is mounted in the module. The first nozzle 127*a* may be mounted to the housing 320 within the recess 320*a*, in a manner similar to that in the previously described embodiment. The first nozzle 127*a* may be operably connected to the other elements of the sanitizer dispensing mechanism 127 as previously described.

Referring again to FIGS. 2A-2B, in certain embodiments, one or more additional nozzles 127*e* may be incorporated into the sanitizer dispensing mechanism 127 to enhance coverage of the door handle 206. For example, the embodiment shows a second nozzle 127*e* coupled to the vehicle door panel 208 and structured to discharge a sanitizing material onto a lowermost exterior surface 206*u* of the door handle 206. The lowermost exterior surface 206*u* of the door handle 206 may be a surface of the door handle 206 closest to a ground surface on which the vehicle 100 rests. To this end, the second nozzle 127*e* may be positioned so that it may be pointed toward the door handle 206 at an upward but non-vertical angle and structured to dispense sanitizer in an arcuate distribution 206*z* extending over an angle α and configured to cover the lowermost exterior surfaces 206*u* of the door handle 206. In one or more arrangements, the arcuate distribution may also be configured to cover at least a portion of the innermost exterior surface 206*a* of the door handle. FIGS. 2A-2B also show the second nozzle 127*e* incorporated into the door handle module 307 housing of sanitizer dispensing mechanism embodiment 127 shown in the drawings.

Referring to FIG. 1, embodiments of the vehicle door handle sanitizing system as described herein may include a vehicle door handle sanitizing system control module 124 configured to control autonomous operation of the door handle sanitizing system. In embodiments described herein, a memory 112 may be communicably coupled to the processor(s) 110 and may store the vehicle door handle sanitizing system control module 124. The memory may also store other modules 123 for controlling other aspects of vehicle operations. The memory 112 is a random-access memory (RAM), read-only memory (ROM), a hard-disk drive, a flash memory, or other suitable memory for storing the module(s) 123, 124. The module(s) 123, 124 are, for example, computer-readable instructions that when executed by the processor 110, cause the processor(s) 110 to perform the various functions disclosed herein.

The vehicle 100 can include one or more modules, at least some of which are described herein. The modules can be implemented as computer-readable program code that, when executed by processor(s) 110, implement one or more of the various processes described herein. One or more of the modules can be a component of the processor(s) 110, or one or more of the modules can be executed on and/or distributed among other processing systems to which the processor(s) 110 is operably connected. The modules can include instructions (e.g., program logic) executable by one or more processor(s) 110. Alternatively, or in addition, one or more of data store(s) 115 or another portion of the vehicle 100 may contain such instructions.

Generally, a module, as used herein, includes routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module as envisioned by the present disclosure is implemented as an application-specific integrated circuit (ASIC), a hardware component of a system on a chip (SoC), as a programmable logic array (PLA), or as another suitable hardware component that is embedded with a defined configuration set (e.g., instructions) for performing the disclosed functions.

In one or more arrangements, one or more of the modules described herein can include artificial or computational intelligence elements, e.g., neural network, fuzzy logic or other machine learning algorithms. Further, in one or more arrangements, one or more of the modules can be distributed among a plurality of the modules described herein. In one or more arrangements, two or more of the modules described herein can be combined into a single module. The module(s) 123, 124 may be partially or fully autonomous and can be operably connected to communicate with each other and with the other elements of the vehicle, including various vehicle systems 140 and/or individual components thereof.

Referring to FIG. 1A, the vehicle door handle sanitizing system control module 124 may include computer-readable instructions that when executed by the processor(s) 110 cause the processor(s) 110 to control operation of the dispensing mechanism 127 to discharge the sanitizing material onto an exterior surface of the door handle 206 responsive to information received from at least one sensor mounted on the vehicle 100 and in operative communication with the door handle sanitizing system control module 124.

A sanitizer dispensing mechanism 127 as described herein may be mounted to any or all vehicle door assemblies so as to cover multiple associated door handles. In some arrangements, all the exteriorly accessible door handles of the vehicle may be covered by at least one nozzle 127*a* of an associated vehicle door handle sanitizing system. The door handle sanitizing system control module 124 may be configured to individually control operation of multiple sanitizer dispensing mechanisms simultaneously.

In particular examples, the vehicle 100 may include at least one door latch sensor 152 configured to detect when an associated vehicle door 210 is latched. In addition, the door handle sanitizing system control module 124 may include computer-readable instructions that when executed by the processor(s) cause the processor(s) 110 to determine if a predetermined time period has passed since the vehicle door 210 was latched. Latching of the door may occur when the door latch mechanism (i.e., a mechanism designed to keep the door closed, but not locked) is engaged so as to prevent opening of the door 210 unless an associated door handle 206 is operated to disengage the latch mechanism. The door handle sanitizing system control module 124 may also be configured to, responsive to passage of the predetermined time period after the vehicle door was latched, control operation of an associated sanitizer dispensing mechanism 127 to discharge the sanitizing material onto one or more exterior surfaces of the door handle 206 as previously described.

The length of the predetermined time period may be selected so as to help ensure that vehicle occupants intending to use a particular door have either exited or entered the vehicle, and that a door handle 206 associated with the door 210 will not be used again for a period of time. Thus, for example, after passage of a predetermined time period (for example, 30 seconds) after a door has been closed and latched after being opened, the door handle sanitizing system control module 124 may control operation of the pump and/or motor in a sanitizer dispensing mechanism 127 associated with the door handle 206, to dispense sanitizer onto the door handle. The sanitizer applied to the handle should then have dried or evaporated before the door handle is touched again by a user.

In particular examples, the vehicle 100 may include at least one door lock sensor 126 configured to detect when an associated vehicle door 210 is locked. In addition, the door handle sanitizing system control module 124 may include computer-readable instructions that when executed by the processor(s) 110 cause the processor(s) to determine if a predetermined time period has passed since the vehicle door 210 was locked. Locking of the door 210 may occur when a door lock is engaged so actively lock the door so that it may not be opened even if the latch mechanism is disengaged. The door handle sanitizing system control module 124 may also be configured to, responsive to passage of the predetermined time period after the vehicle door was locked, control operation of an associated sanitizer dispensing mechanism 127 to discharge the sanitizing material onto one or more exterior surfaces of the door handle as previously described.

The input system 130 may be configured to enable a user to select various operating parameters (for example, the predetermined time period) of the door handle sanitizing system.

Detailed embodiments are disclosed herein. However, it is to be understood that the disclosed embodiments are intended only as examples. Therefore, specific structural and functional details disclosed herein are not to be interpreted as limiting, but merely as a basis for the claims and as a representative basis for teaching one skilled in the art to variously employ the aspects herein in virtually any appropriately detailed structure. Further, the terms and phrases used herein are not intended to be limiting but rather to provide an understandable description of possible implementations. Various embodiments are shown in FIGS. 1-3B, but the embodiments are not limited to the illustrated structure or application.

The systems, components and/or processes described above can be realized in hardware or a combination of hardware and software and can be realized in a centralized fashion in one processing system or in a distributed fashion where different elements are spread across several interconnected processing systems. Any kind of processing system or another apparatus adapted for carrying out the methods described herein is suited. A typical combination of hardware and software can be a processing system with computer-usable program code that, when being loaded and executed, controls the processing system such that it carries out the methods described herein. The systems, components and/or processes also can be embedded in a computer-readable storage, such as a computer program product or other data programs storage device, readable by a machine, tangibly embodying a program of instructions executable by the machine to perform methods and processes described herein. These elements also can be embedded in an application product which comprises all the features enabling the implementation of the methods described herein and, which when loaded in a processing system, is able to carry out these methods.

Generally, modules as used herein include routines, programs, objects, components, data structures, and so on that perform particular tasks or implement particular data types. In further aspects, a memory generally stores the noted modules. The memory associated with a module may be a buffer or cache embedded within a processor, a RAM, a ROM, a flash memory, or another suitable electronic storage medium. In still further aspects, a module, as envisioned by the present disclosure, is implemented as an application-specific integrated circuit (ASIC), a hardware component of a system on a chip (SoC), as a programmable logic array (PLA), or as another suitable hardware component that is embedded with a defined configuration set (e.g., instructions) for performing the disclosed functions.

Program code embodied on a computer-readable medium may be transmitted using any appropriate medium, including but not limited to wireless, wireline, optical fiber, cable, RF, etc., or any suitable combination of the foregoing. Computer program code for carrying out operations for aspects of the present arrangements may be written in any combination of one or more programming languages, including an object-oriented programming language such as Java™, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The terms "a" and "an," as used herein, are defined as one or more than one. The term "plurality," as used herein, is defined as two or more than two. The term "another," as used herein, is defined as at least a second or more. The terms "including" and/or "having," as used herein, are defined as comprising (i.e., open language). The phrase "at least one of . . . and . . . " as used herein refers to and encompasses any and all possible combinations of one or more of the associated listed items. As an example, the phrase "at least one of A, B, and C" includes A only, B only, C only, or any combination thereof (e.g., AB, AC, BC or ABC).

Aspects herein can be embodied in other forms without departing from the spirit or essential attributes thereof. Accordingly, reference should be made to the following claims, rather than to the foregoing specification, as indicating the scope hereof.

What is claimed is:

1. A vehicle door assembly comprising:

a vehicle door panel;

a vehicle door handle operably connected to the door panel so as to enable operation of a door latch by the door handle; and at least one sanitizer dispensing mechanism having at least a first nozzle coupled to the vehicle door panel and structured to discharge a sanitizing material onto an exterior surface of the door handle, wherein the at least a first nozzle is structured to reside at a level vertically higher than the door handle when the vehicle door assembly is mounted on a vehicle, and wherein the at least a first nozzle is structured to dispense the sanitizing material in an arcuate distribution from the at least a first nozzle along a horizontal plane located above the door handle when the vehicle door assembly is mounted on the vehicle.

2. The vehicle door assembly of claim 1 wherein the at least a first nozzle is an atomizer structured to dispense a fine mist of sanitizing material.

3. The vehicle door assembly of claim 1 wherein the at least a first nozzle is positioned along a vertical plane bisecting a length of the door handle.

4. The vehicle door assembly of claim 1 wherein the vehicle door panel includes a recess structured to receive at least a portion of the door handle therein and wherein the at least a first nozzle is mounted within the recess.

5. The vehicle door assembly of claim 1 wherein the at least a first nozzle is structured to dispense the sanitizing material onto an uppermost exterior surface of the door handle.

6. The vehicle door assembly of claim 1 wherein the at least a first nozzle is structured to dispense the sanitizing material onto an outermost exterior surface of the door handle.

7. The vehicle door assembly of claim 1 wherein the at least a first nozzle is structured to dispense the sanitizing material onto an innermost exterior surface of the door handle.

8. The vehicle door assembly of claim 1 wherein the vehicle door panel includes an opening formed therein, wherein the door assembly includes a door handle module structured to be secured in the opening, the door handle module including a recess structured to receive the at least a portion of the door handle therein.

9. The vehicle door assembly of claim 1 further comprising a second nozzle coupled to the vehicle door panel and structured to discharge a sanitizing material onto a lowermost exterior surface of the door handle.

10. The vehicle door assembly of claim 9 wherein the second nozzle is structured to dispense the sanitizing material onto an innermost exterior surface of the door handle.

11. The vehicle door assembly of claim 1 wherein the vehicle door assembly is mounted on a vehicle, the vehicle including one or more processors and a memory communicably coupled to the one or more processors and storing a vehicle door handle sanitizing system control module including computer-readable instructions that when executed by the one or more processors cause the one or more processors to control operation of the at least one dispensing mechanism to discharge the sanitizing material onto an exterior surface of the door handle responsive to information received from at least one sensor mounted on the vehicle and in operative communication with the door handle sanitizing system control module.

12. The vehicle door assembly of claim 11 wherein the vehicle includes at least one door latch sensor configured to detect when the vehicle door is latched and wherein the control module includes computer-readable instructions that when executed by the one or more processors cause the one or more processors to:

determine if a predetermined time period has passed since the vehicle door was latched; and responsive to passage of the predetermined time period after the vehicle door was latched, control operation of the at least one dispensing mechanism to discharge the sanitizing material onto the exterior surface of the door handle.

13. The vehicle door assembly of claim 11 wherein the vehicle includes at least one door lock sensor configured to detect when the vehicle door is locked and wherein the control module includes computer-readable instructions that when executed by the one or more processors cause the one or more processors to:

determine if a predetermined time period has passed since the vehicle door was locked; and responsive to passage of the predetermined time period after the vehicle door was locked, control operation of the at least one dispensing mechanism to discharge the sanitizing material onto the exterior surface of the door handle.

14. A vehicle door assembly comprising:

a vehicle door panel;

a vehicle door handle operably connected to the door panel so as to enable operation of a door latch by the door handle; and at least one sanitizer dispensing mechanism having at least a first nozzle coupled to the vehicle door panel and structured to discharge a sanitizing material onto an exterior surface of the door handle, wherein the vehicle door assembly is mounted on a vehicle, the vehicle including one or more processors and a memory communicably coupled to the one or more processors and storing a vehicle door handle sanitizing system control module including computer-readable instructions that when executed by the one or more processors cause the one or more processors to control operation of the at least one dispensing mechanism to discharge the sanitizing material onto an exterior surface of the door handle responsive to information received from at least one sensor mounted on the vehicle and in operative communication with the door handle sanitizing system control module, and wherein the vehicle includes at least one door lock sensor configured to detect when the vehicle door is locked and wherein the control module includes computer-readable instructions that when executed by the one or more processors cause the one or more processors to:

determine if a predetermined time period has passed since the vehicle door was locked; and responsive to passage of the predetermined time period after the vehicle door was locked, control operation of the at least one dispensing mechanism to discharge the sanitizing material onto the exterior surface of the door handle.

* * * * *